United States Patent [19]

Miyanaga et al.

[11] Patent Number: 5,238,526
[45] Date of Patent: Aug. 24, 1993

[54] METHOD OF FORMING CHARGE TRANSFER COMPLEXES

[75] Inventors: Akiharu Miyanaga, Kawasaki; Masashi Hongoh, Atsugi, both of Japan

[73] Assignee: Semiconductor Energy Laboratory Co., Ltd., Kanagawa, Japan

[21] Appl. No.: 586,148

[22] Filed: Sep. 21, 1990

[30] Foreign Application Priority Data

Sep. 26, 1989 [JP] Japan .................................. 1-249906

[51] Int. Cl.$^5$ ............................................ C30B 23/02
[52] U.S. Cl. .................................. 156/610; 156/611; 156/DIG. 113
[58] Field of Search ...... 156/610, 611, 902, DIG. 113; 357/8; 437/1

[56] References Cited

FOREIGN PATENT DOCUMENTS 0229971 8/1987 Japan .......................................... 437/1
0233778 9/1989 Japan .......................................... 357/8

OTHER PUBLICATIONS

Yase et al, Epi Growth of a highly conductive charge trans. complex from vapor phase TTF-TCNQ, Bulletin of Inst. for Chem. Research (vol. 62, No. 4) Kyoto Univ., Japan, Jul. 1984, pp. 242-250.
Kawabata et al., "Conducting Thin Films of α-(BED-T-TTF)$_2$I$_3$ by Evaporation Method", Solid State Communications, vol. 74, No. 2, pp. 83-86, 1990.
Brice, Crystal Growth Processes, John Wiley and Sons, New York 1986, 242-243.
Pamplin, Crystal Growth second edition Pergamon Press, New York, 1980 pp. 227-229.

*Primary Examiner*—Robert Kunemund
*Attorney, Agent, or Firm*—Sixbey Friedman Leedom & Ferguson

[57] ABSTRACT

A charge transfer complex of donor and acceptor molecules is formed through a vapor phase reaction. After the formation, the complex is subjected to thermal annealing in order to optimize the proportion of the donor and the acceptor. By this method, the formation speed is significantly increased.

13 Claims, 2 Drawing Sheets

METHOD OF FORMING CHARGE TRANSFER COMPLEXES

BACKGROUND OF THE INVENTION

The present invention relates to a method of forming complexes, and more paricularly relates to a method of forming organic charge transfer complexes.

Research has been carried out into formation of charge transfer complexes of low molecular compounds and at the present time many such complexes have been obtained. In such complexes electric charge is exchanged between constituent donor molecules (represented simply by D) supplying electrons and constituent acceptor molecules (represented simply by A) receiving electrons. Some complexes can be formed with high conductivities depending upon the amount of charge transferred.

Among usuful acceptor molecules are TCNQ (tetracyanoquinodimethane) and derivatives thereof, for example;

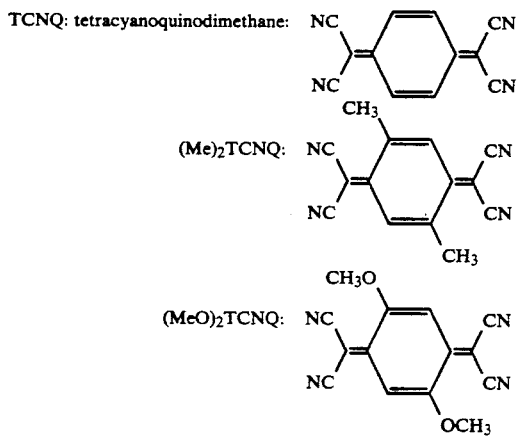

These molecules have been known to possess large electron affinities and form charge transfer complexes with many donor molecules. Similar molecules are as follow:

The acceptor molecules of this kind are called generally TCNQ-based molecules.

Among usuful donor molecules in turn are, for example:

TTF: tetrathiafulvalene

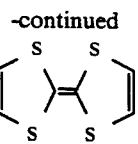

TMTTF: tetramethyltetrathiafulvalene

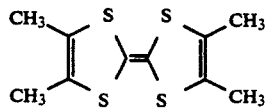

TSF: tetraselenafulvalene

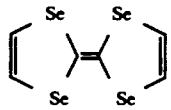

TMTSF: tetramethyltetraseleafulvalene

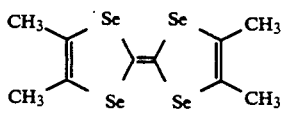

The donor molecules of this kind are called simply TTF-based molecules. In the molecular structures of TTF-based molecules and TCNQ-based molecules, central atoms are arranged in a plane constituting the backbone of the molecule (called here the molecular plane). A number of $\pi$ electrons existing in the molecular plane play determinant functions for the characteristics of the substance.

Electron transfer complexes can be obtained by combining suitable donor and acceptor molecules, for example, by combining the above described TTF-based and TCNQ-based molecules such as $(TTF)_x(TCNQ)_y$, $(TMTTF)_x(TCNQ)_y$, $(TSF)_x(TCNQ)_y$ and $(TMTSF)_x(TCNQ)_y$. Several tens or thousands S/cm of conductivity may be achieved by selecting suitable preparation methods.

In order to form metallic phases having such high conductivity, there are two requirements as follow. First, the ratio between x and y in $D_xA_y$ has to be adjusted at an optimum value by, e.g. eliminating impurities to avoid disturbance of crystalline structure due to the existence of impurities. In the case of (TTF-based molecule)$_x$(TCNQ-based molecule)$_y$, the ratio has to be adjusted so that x:y=1:1 in order to obtain desired black metallic complexes while complexes becomes a semiconductor at x:y=1.3:2 or 1.66:2. Second, donor molecules and acceptor molecules have to be arranged into a "separated laminate" in which donor and acceptor molecules are laminated in different planes which are not parallel with each other as illustrated in FIG. 1(A). In the figure, solid lines represent the molecular planes of respective molecules. When a complex is prepared in this laminate structure, there are formed separate molecular columns consisting of donor molecules and acceptor molecules respectively. The molecular columns form current paths respectively in the complex so that its conductivity can be increased. For this reason, it is very important point for obtaining complexes having high conductivities to construct crystalline structures selectively into the separated laminate.

Several attempts have been made to form charge transfer complexes. Many of them generally utilize liquid state reactions of solvents such as diffusion methods or electric field methods. The preparation time required to form complexes in such conventional methods, however, is very long, for example, several months or longer in the case of the diffusion method. When prepared in such a long time, donor molecules and acceptor molecules are arranged into an overlapping laminate in which the donor molecules and acceptor molecules are arranged in parallel and partially and alternately overlapped, rather than the separated laminate, as illustrated in FIG. 1(B). This is because the overlapping laminate constitutes the stable state of the complex while the separated laminate constitutes only a metastable state.

For example, it has been reported that, even if $(TMTSF)_x(TCNQ)_y$ was formed by a liquid phase diffusion at x:y= 1:1, only reddish crystals corresponding to the overlapping laminate were formed when a long formation time was spent while black crystals corresponding to the separated laminate were obtained when the formation time was relatively short. From these considerations, it seems preferred to decrease the time spent for the formation of complexes in order to achieve high conductivities.

There are some exceptions that complexes having relatively high conductivities are formed in fact even by conventional liquid phase methods. For example, $(TMTTF)_x(TCNQ)_y$ can be formed in a metallic phase with black crystalline appearance at x:y=1:1 by a liquid phase method. This is, however, hardly applicable for commercialization (mass-production) since the preparation time is too long, several months or longer in the case of usual liquid diffusion methods as described above. When prepared within a shorter time, the product of complexes assume only the form of microcrsytals which can be utilized for few applications. In addition, the control of complex crystal formation is too difficult to reproduce appropriate separated laminates required to realize sufficient conductivities for applications.

BRIEF SUMMARY OF THE INVENTION

It is an object of the present invention to provide a method of manufacturing charge transfer metallic complexes with ease.

It is another object to form a large amount of charge transfer complex $D_xA_y$ at a high speed suitable for mass production so that D and A are separataly laminated.

Additional objects, advantages and novel features of the present invention will be set forth in the description which follows, and in part will become apparent to those skilled in the art upon examination of the following or may be learned by practice of the present invention. The object and advantages of the invention may be realized and attained by means of the instrumentalities and combinations particularly pointed out in the appended claims.

To achieve the foregoing and other objects, and in accordance with the present invention, as embodied and broadly described herein, the basic structure of the separated laminate of the complex is constructed in a vapor phase, followed by an annealing process to eliminate unnecessary substances from the basic structure and make the laminate perfect.

In a first step, the basic structure of the separated laminate comprising donor molecules D and acceptor molecules A of a charge transfer complex $D_xA_y$ is constructed in a vapor phase. This step is carried out by a direct vapor phase reaction such as a sublimating or a melting evaporation method. A donor source material and acceptor molecules may be disintegrated (sublimated) concurrently or alternately. In a particular case, a precursor material is prepared by conducting a reaction between donor and acceptor in advance, and the precursor material is used as a single source of the vapor phase reaction.

Both a donor and an acceptor source material are preferably purified in advance of the actual preparation of a charge transfer complex. This treatment is necessary to obtain complex crystals having a high purity. The high purity obtained by purification of an organic substance is lowered in general only by continuing exposure to air and therefore the purification has to be carried out just before the vapor phase reaction. Some of donor or acceptor candidates decompose at a temperature lower than their sublimation or melting evaporation temperatures. The present invention can not be applied to such donor of acceptor candidates of within the teaching of this description without a further improvement. It is ascertained in the purification process whether or not the candidates can be used.

The complex crystals thus formed are annealed at an appropriate temperature, at which thermal decomposition thereof shall not take place, for example, at 100°~150° C. or a lower temperature, for several hours in order to eliminate contaminants and optimize x and y in $D_xA_y$ for the purpose of making the crystallization perfect. This annealing is carried out at a reduced pressure (approx. 10 Torr or lower) or in an atmosphere of an inactive gas such as Ar and $N_2$.

The values of x and y in $D_xA_y$ approach target values (1:1) as the annealing time increases. Depending upon the complex, however, the molecular structure thereof may be converted from the separated laminate to the overlapping laminate structure when the annealing at a high temperature is continued for a long time. Usually, the annealing time is up to 10 hours. Usable crystals can be formed only by 1 hour annealing in some cases. The annealing is preferably carried out in an apparatus which is designed not to allow unnecessary substances removed from the crystals to get mixed therewith again.

The crystals thus obtained are small black single crystals or polycrystalline films. The values of x and y in $D_xA_y$ are optimized so that high conductivities are exhibited.

BRIEF DESCRIPTION OF THE DRAWINGS

The accompanying drawings, which are incorporated in and form a part of the invention and, together with the description, serve to explain the principles of the invention.

DETAILED DESCRIPTION OF THE PREFERRED EMBODIMENTS

Figure 1A:
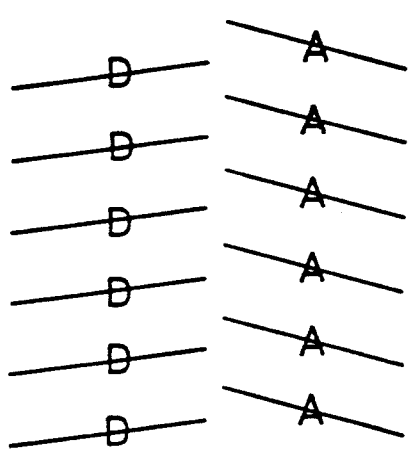
FIG. 1(A) is a schematic diagram showing molecular arrangement in accordance with a separated laminate.
Figure 1B:
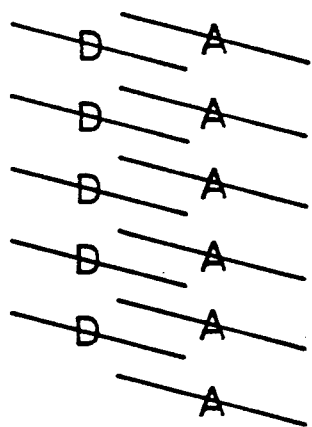
FIG. 1(B) is a schematic diagram showing molecular arrangement in accordance with an overlapping laminate.

Referring now to the drawings, which illustrate an apparatus suitable for carrying out vapor phase reaction, a method of preparing charge transfer complexes in accordance with an first embodiment of the invention will be described. The apparatus comprises a reaction tube 1, retainers 5 and 6 provided inside of the tube 1, teflon substrates 8 attached to the inside of the tube 1, a ceramic cylinder 2 supporting the reaction tube 1, an electric heater 3 surrounding the cylinder 2 and a chromel-alumer thermocouple 7. The reaction tube 1 and the retainers 5 and 6 are made from pyrex glass. The locations of the substrates 8 and the retainers 5 and 6 and a suitable temperature to be detected by the thermocouple 7 are determined in accordance with the sublimation temperatures of the donor and acceptor source materials to be put in the retainers 5 and 6 and the complex to be sublimated on the substrates 8 with reference to the temperature gradient in the vertical direction. Examples of sublimation temperatures of donors and acceptors are as follows:

TTF: 111° C. (5 mmHg), TMTTF: 157° C. (5 mmHg), TMTSF: 164° C. (3 mmHg), TCNQ: 180° C. (11 mmHg)

After putting donor and acceptor source materials respectively in the retainers 5 and 6 and evacuating the inside of the tube 1 to an appropriate pressure, the tube 1 was hermetically closed and heated by means of the heater 3. The heating was continued approximately for an hour. As a result, $D_xA_y$ complex crystals of 100~200 μm width and 1 mm height were grown on the teflon substrates 8. The total weight of the crystals were approximately 100 mg.

The $D_xA_y$ complex crystals thus formed were conductive but exhibited characteristics of a semiconductor with a ratio of $x:y \neq 1:1$. These crystals were thermal annealed at 100°~150° C. for 2 hours in a muffle furnace. Then, desired charge transfer complexes were obtained whose electric conductivities are shown below.

TTF·TCNQ: 500 S/cm, TMTTF·TCNQ: 60 S/cm, TSF·TCNQ: 5200 S/cm, TMTSF·TCNQ: 100 S/cm

Figure 2:
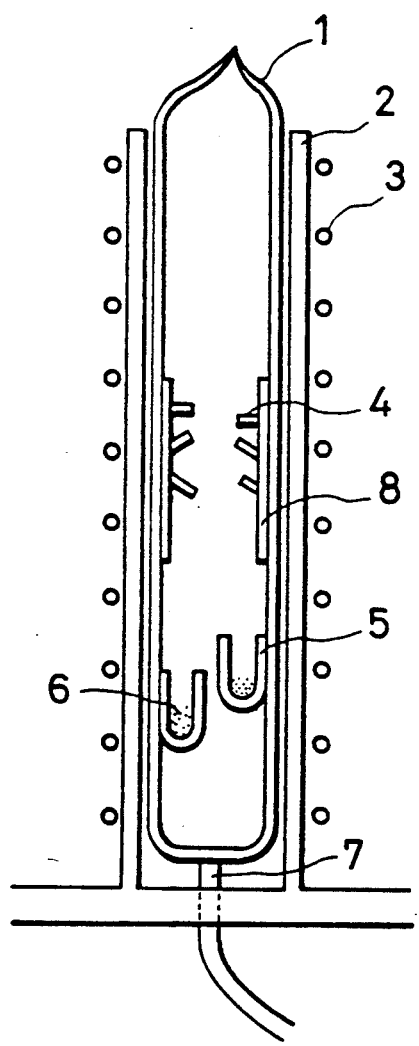
FIG. 2 is a cross sectional view showing an apparatus for vapor phase reaction suitable for methods in accordance with a first embodiment of the present invention.

Although in the above example the tube 1 was hermetically sealed off, the donor and acceptor can be supplied into an open tube in fluid forms from bubbling devices in which liquids containing donor and acceptor sources respectively are bubbled by an inert gas. The fluid donor and acceptor sources are mixed in the open tube so that complex crystals are grown on the substrate. Although in the structure shown in FIG. 2 the substrate on which crystals grow is located to be heated, the location may be a cooling location in some particular cases.

Figure 3:
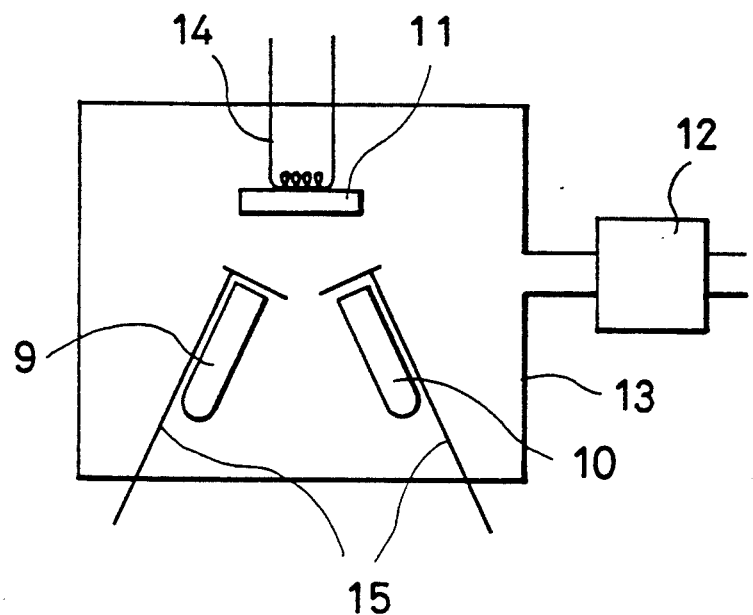
FIG. 3 is a cross sectional view showing an apparatus for vapor phase reaction suitable for methods in accordance with a second embodiment of the present invention.

Referring to FIG. 3, a second embodiment of the present invention will be described. The figure illustrates a vapor reaction apparatus comprising a vacuum chamber 13, a rotary pump 12 connected to the chamber 13, a teflon substrate 11 provided with a heater 14 in the chamber 13 and retainers 9 and 10. The retainers 9 and 10 are also provided with built-in heaters and chromel-alumer thermocouples to achieve appropriate temperatures. TTF or TMTT as a donor source and TCNQ as an acceptor were put in the retainers 9 and 10. The inside of the chamber 13 was evacuated by means of the rotary pump 12 to a pressure of no higher than 1 Torr. Crystals of $D_xA_y$ were grown on the substrate 11 by heating the retainers 9 and 10. The ratio of x:y was controlled by regulating the opening of shutters 15 provided on the apertures of the retainers 9 and 10 as well as by adjusting the temperature of the retainer 9 and 10. The temperature of the retainer 9 and 10 was determined with reference to the sublimation temperatures of the donor and acceptor. The opening of each shutter 15 was controlled by an automatic regulating device in terms of how many times the shutter was opened per minute. The shutter is opened for about one second at a time. During the formation of crystals, the temperature of the substrate 11 was maintained at a cerain temperature selected between room temperature and 80° C., which temperature was changed through samples for investigation. The temperatures of retainers 9 and 10 and the substrate 11 were detected by means of a chromel-alumer thermocouple.

Through the experiments, it has been known that the suitable temperature of the substrate 11 is between 25° C. and 40° C. At a lower temperature than this range, the crystallization speed decreased and the size of crystals was reduced. The appropriate opening time (total time) of the retainer 9 holding the acceptor was equal to or about 10% shorter than that of the other retainer 10 holding the donor. At an appropriate condition thus determined, a large number of black complex crystals were grown to 1 mm or near 1 mm height by 60~120 minutes process. The ratio of x:y was near 1:1. The conductivity was relatively high while some semiconductive nature appeared.

The crystal thus formed were sujected to thermal annealing in an incubator through which nitrogen was passed. After the annealing continued for 5 hours at 300° C. The ratio of x:y was improved to be just 1:1. The conductivities were measured to be 600 S/cm (TTF·TCNQ) and 70 S/cm (TMTTF·TCNQ). The structures of these crystals are considered to be of a complete separated laminate.

A method in accordance with a third embodiment of the present invention was carried out also by use of the apparatus illustrated in FIG. 3. The heater 14, however, was replaced by another heater capable of heating the substrate to about 150° C. In this embodiment, the formation of complex crystals was carried out in the same manner as in the second embodiment except that the annealing process was carried out in the vacuum chamber 13 without transportation of the complex crystals at 100° C. or lower temperatures for three hours and that TMTSF was used instead of TMTTF. The conductivities were measured to be 100 S/cm (TTF·TCNQ) and 200 S/cm (TMTTF·TCNQ). In regard to TMTTF·TCNQ, when the annealing temperature was lower than 100° C. the conductivity was slightly higher than that achieved at 100° C. In accordance with this embodiment, it was prevented that impurities influenced upon the separated laminate structure during transportation of the complex crystals from the crystal formation stage to the thermal annealing stage.

Figure 4:
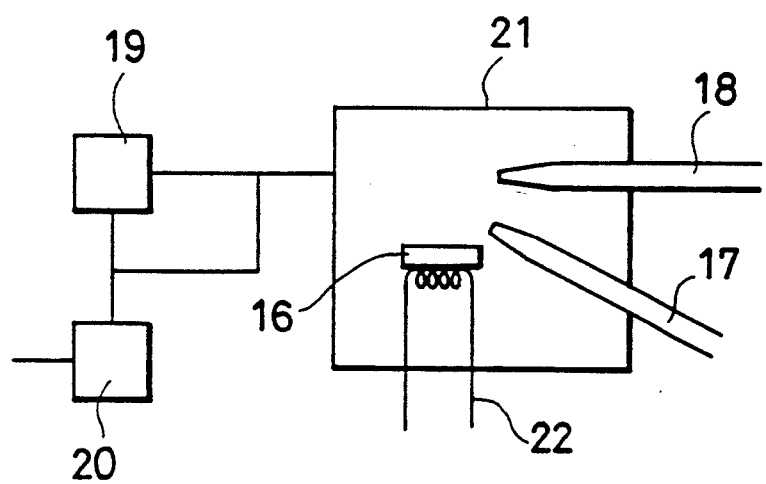
FIG. 4 is a cross sectional view showing an apparatus for thermal annealing suitable for methods in accordance with a fourth embodiment of the present invention.

Next, a fourth embodiment will be described. The formation of complex crystals of this embodiment was carried out in the same manner as in accordance with the second embodiment except that TMTSF was used instead of TMTTF. The thermal annealing was carried out in an annealling apparatus as illustrated in FIG. 4. The annealing apparatus comprises a vacuum chamber 21, a rotary pump 20 and a diffusion pump 19 connected to the vacuum chamber 21, a substrate provided with a heater 22 in the chamber 21 and a pair of jet nozzles 18 and 17 inserted into the inside of the chamber toward the substrate 16. After transporting the complex crystals together with the substrate 8 from the apparatus shown in FIG. 3 to the upper surface of the substrate 16, the chamber was evacuated to 0.1 Torr or a lower pressure followed by heating the substrate 16° to 100° C. The annealing was continued for an hour. During the annealing, a jet of an inactive gas was caused to blow impurities which come out from the crystals by the annealing effect. In order to avoid the undesirable direct influence of the jet upon the crystals, the distances between the crystals and the end of each of the nozzles 17 and 18 were selected no shorter than 1 cm. In accordance with this embodiment, it was prevented that undesirable influence of impurities coming out from the complex crystals during thermal annealing was exerted upon the separated laminate structure. As a result, a large number of black complex crystals were grown to approximately 1 mm with the ratio of x:y=1. The conductivities were measured to be 400 S/cm (TTF·TCHQ) and 150 S/cm (TMTTF·TCNQ).

The foregoing description of preferred embodiments has been presented for purposes of illustration and description. It is not intended to be exhaustive or to limit the invention to the precise form described, and obviously many modifications and variations are possible in light of the above teaching. The embodiment was chosen in order to explain most clearly the principles of the invention and its practical application thereby to enable others in the art to utilize most effectively the invention in various embodiments and with various modifications as are suited to the particular use contemplated. Although the supplying of amounts of donor and acceptor are controlled by provision of shutters, the opening size of the aperture of each retainer may be adjusted in advance in order to obtain the 1:1 ratio.

What is claimed is:

1. A method of forming a charge transfer complex of a donor and an acceptor, said method comprising:
    forming crystals of the complex of said donor and acceptor on a substrate through a vapor phase reaction; and
    thermally annealing said crystals in order to remove contaminants and optimize the proportion of said donor and acceptor in said complex.

2. The method of claim 1 wherein said forming step comprising disintegrating a solid state source of said donor and acceptor into a form of vapor at an elevated temperature and growing crystals of said complex from said vapor.

3. The method of claim 2 wherein said forming step comprising disposing said solid state source in a vacuum chamber, heating said solid state source to produce said vapor and growing crystals of said complex on said substrate.

4. The method of claim 3 wherein said source comprising a donor source material and an acceptor source material contained in separate retainers having apertures.

5. The method of claim 1 wherein said donor is TTF, TMTTF, TSF or TMTSF.

6. The method of claim 1 wherein said acceptor is TNAP, TCNDQ or TCNQ or its derivative.

7. The method of claim 1 wherein said complex is $(TTF)_x(TCNQ)_y$, $(TMTTF)_x(TCNQ)_y$, $(TSF)_x(TCNQ)_y$ or $(TMTSF)_x(TCNQ)_y$.

8. The method of claim 1 wherein said forming step comprising bubbling liquids containing said donor and said acceptor with an inactive gas and heating said inactive gas carrying said donor and acceptor to carry out said vapor phase reaction.

9. The method of claim 1 wherein said substrate is made of teflon.

10. The method of claim 1 wherein said forming step is carried out in a vacuum chamber followed by said annealing step in the same vacuum chamber by heating said substrate.

11. The method of claim 1 wherein the surfaces of said crystals are swept by blowing an inactive gas during said annealing step.

12. The method of claim 1 wherein the deposited complex is heated to a temperature at which said complex does not decompose during said annealing step.

13. The method of claim 12 wherein the temperature at which said annealing is carried out is 100° to 150° C.

* * * * *